United States Patent
Zizi

(10) Patent No.: US 9,690,904 B1
(45) Date of Patent: Jun. 27, 2017

(54) SIGNAL-EMBEDDED SIGNATURES

(71) Applicant: SCANADU INCORPORATED, Moffett Field, CA (US)

(72) Inventor: Martin Zizi, Enines (BE)

(73) Assignee: Scanadu Incorporated, Sunnyvale, CA (US)

(*) Notice: Subject to any disclaimer, the term of this patent is extended or adjusted under 35 U.S.C. 154(b) by 38 days.

(21) Appl. No.: 14/612,287

(22) Filed: Feb. 2, 2015

Related U.S. Application Data

(63) Continuation-in-part of application No. 14/292,820, filed on May 30, 2014.

(60) Provisional application No. 61/937,437, filed on Feb. 7, 2014, provisional application No. 61/924,230, filed on Jan. 6, 2014, provisional application No. 61/875,681, filed on Sep. 9, 2013.

(51) Int. Cl.
A61B 5/0402 (2006.01)
G06F 21/32 (2013.01)
G06F 19/00 (2011.01)
H04B 15/00 (2006.01)
A61B 5/00 (2006.01)
A61B 5/117 (2016.01)

(52) U.S. Cl.
CPC .......... *G06F 19/3406* (2013.01); *A61B 5/117* (2013.01); *A61B 5/6898* (2013.01); *G06F 19/322* (2013.01); *H04B 15/005* (2013.01)

(58) Field of Classification Search
None
See application file for complete search history.

(56) References Cited

U.S. PATENT DOCUMENTS

| | | | | |
|---|---|---|---|---|
| 7,689,833 B2* | 3/2010 | Lange | ............... | A61B 5/04525 382/115 |
| 8,696,569 B2* | 4/2014 | Yuen | ................... | G06F 19/3418 128/920 |
| 8,886,316 B1* | 11/2014 | Juels | ................. | A61N 1/37252 607/30 |
| 8,994,498 B2* | 3/2015 | Agrafioti | ................. | G06F 21/40 340/5.52 |
| 9,426,139 B1* | 8/2016 | McClintock | ............ | H04L 63/08 |
| 9,450,961 B2* | 9/2016 | Stanasolovich | ........... | G06F 3/00 |
| 2003/0078693 A1* | 4/2003 | Chavez | ................ | G06Q 10/087 700/237 |
| 2003/0103653 A1* | 6/2003 | Avni | ....................... | G06F 21/32 382/119 |
| 2004/0059950 A1* | 3/2004 | Bender | ................ | G06F 21/316 726/5 |
| 2009/0072985 A1* | 3/2009 | Patel | ...................... | H04B 3/544 340/657 |
| 2013/0063550 A1* | 3/2013 | Ritchey | ................. | G03B 37/00 348/36 |

(Continued)

*Primary Examiner* — Kennedy Schaetzle
(74) *Attorney, Agent, or Firm* — Alford Law Group, Inc.; William E. Alford

(57) ABSTRACT

In accordance with one embodiment, a method for a health scanning system is disclosed. The method includes receiving at least one electrical physiological data signal (PDS); suppressing a Direct Current (DC) signal component of the PDS to emphasize the Alternating Current (AC) signal component of the PDS; isolating the signal noise in the AC signal component of the PDS; and extracting a noise signature from the signal noise in the PDS. The noise signature, after calibration, can be used to uniquely identify a known user from other users.

9 Claims, 13 Drawing Sheets

(56) References Cited

U.S. PATENT DOCUMENTS

| | | | | |
|---|---|---|---|---|
| 2014/0188770 | A1* | 7/2014 | Agrafioti | A61B 5/117 706/13 |
| 2015/0006115 | A1* | 1/2015 | Svoboda | G01D 3/08 702/190 |
| 2015/0128240 | A1* | 5/2015 | Richards | H04L 63/0861 726/7 |
| 2015/0379989 | A1* | 12/2015 | Balasubramanian | G06Q 30/0255 704/233 |
| 2016/0011004 | A1* | 1/2016 | Matsumoto | G01C 21/16 702/96 |
| 2016/0231830 | A1* | 8/2016 | Nemala | G06F 3/038 |

* cited by examiner

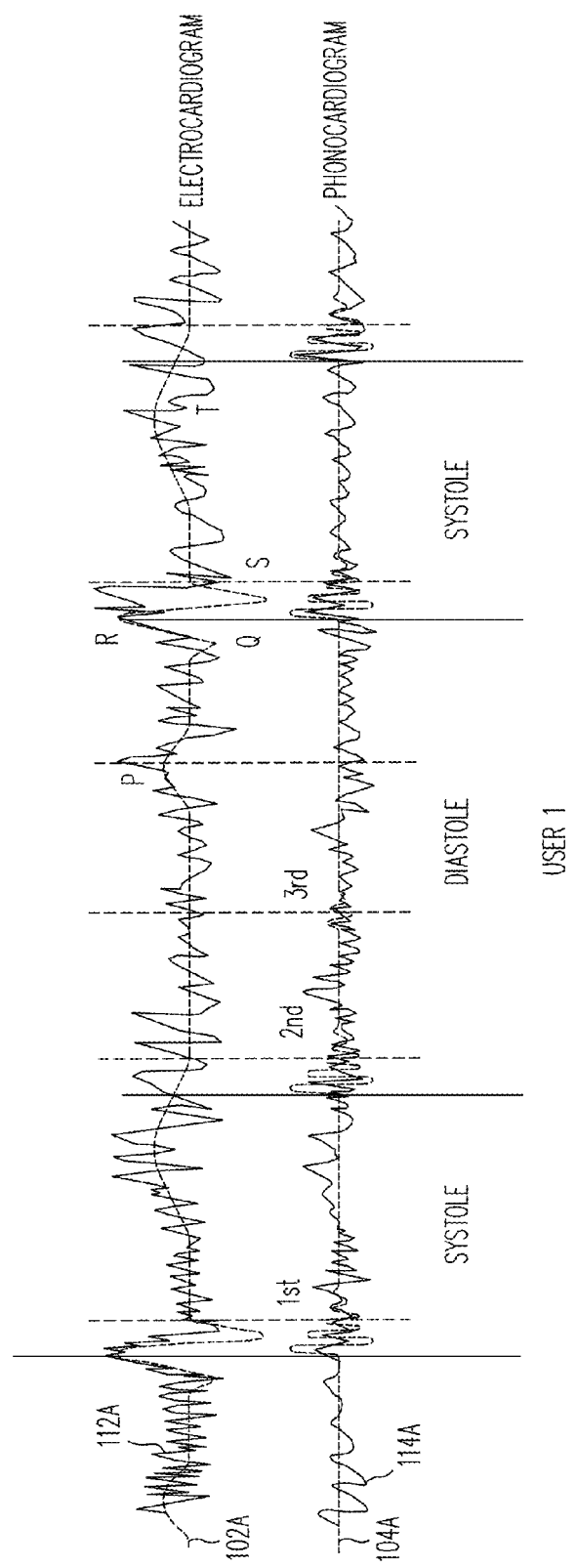

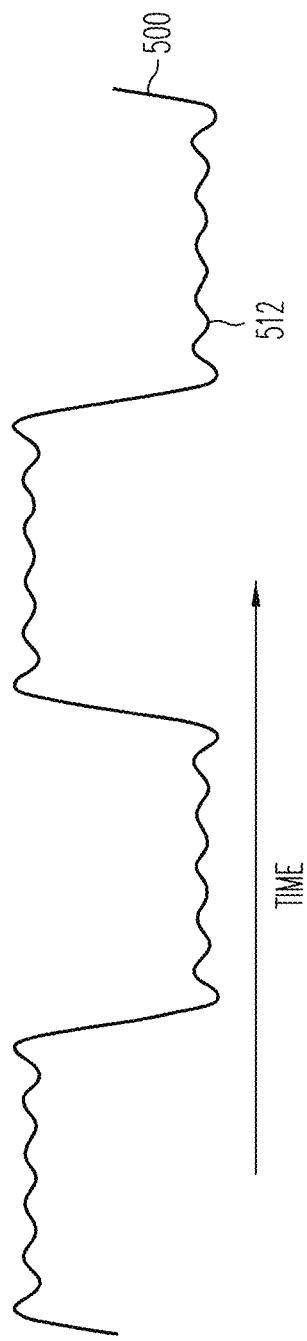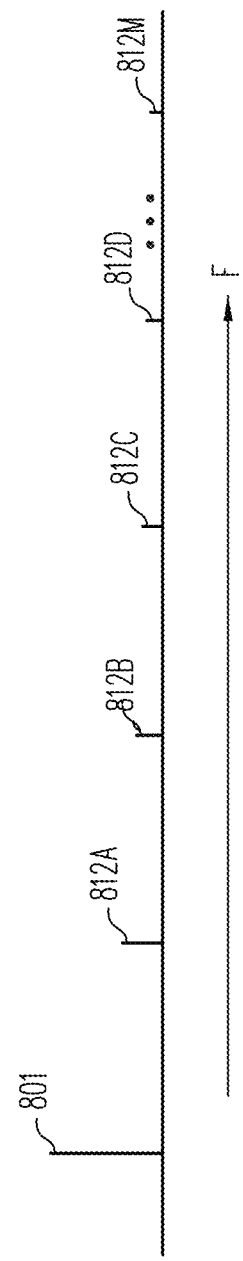

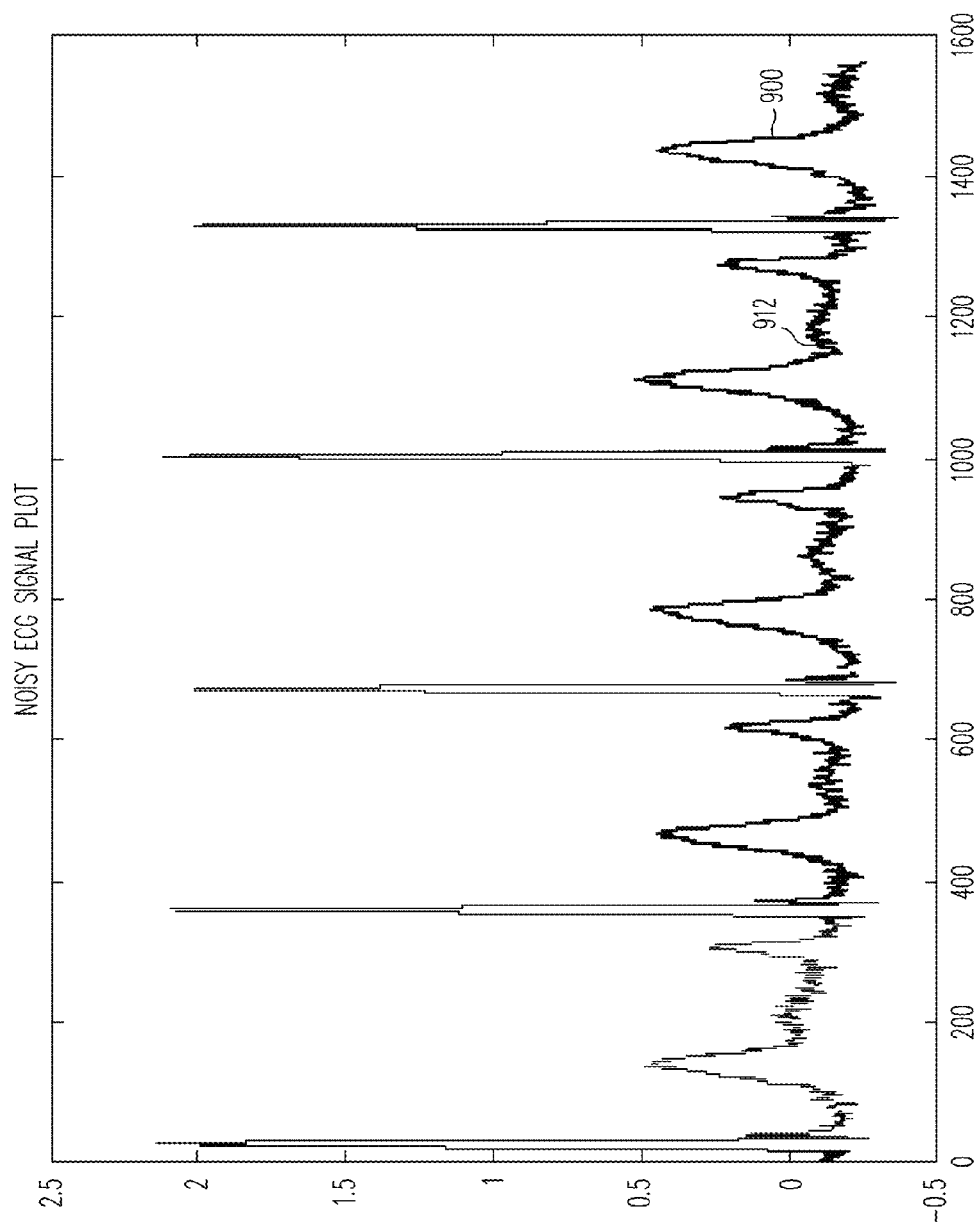

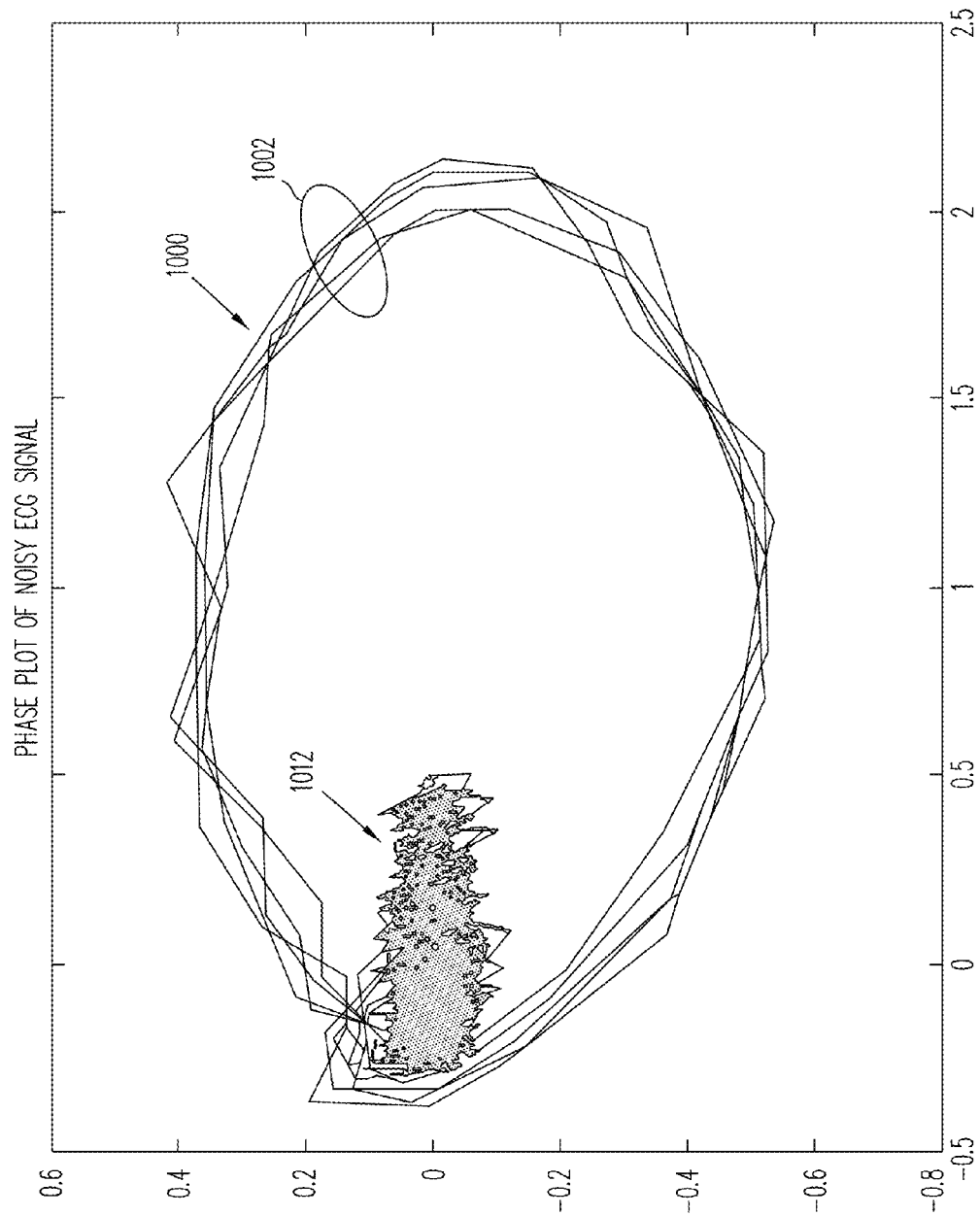

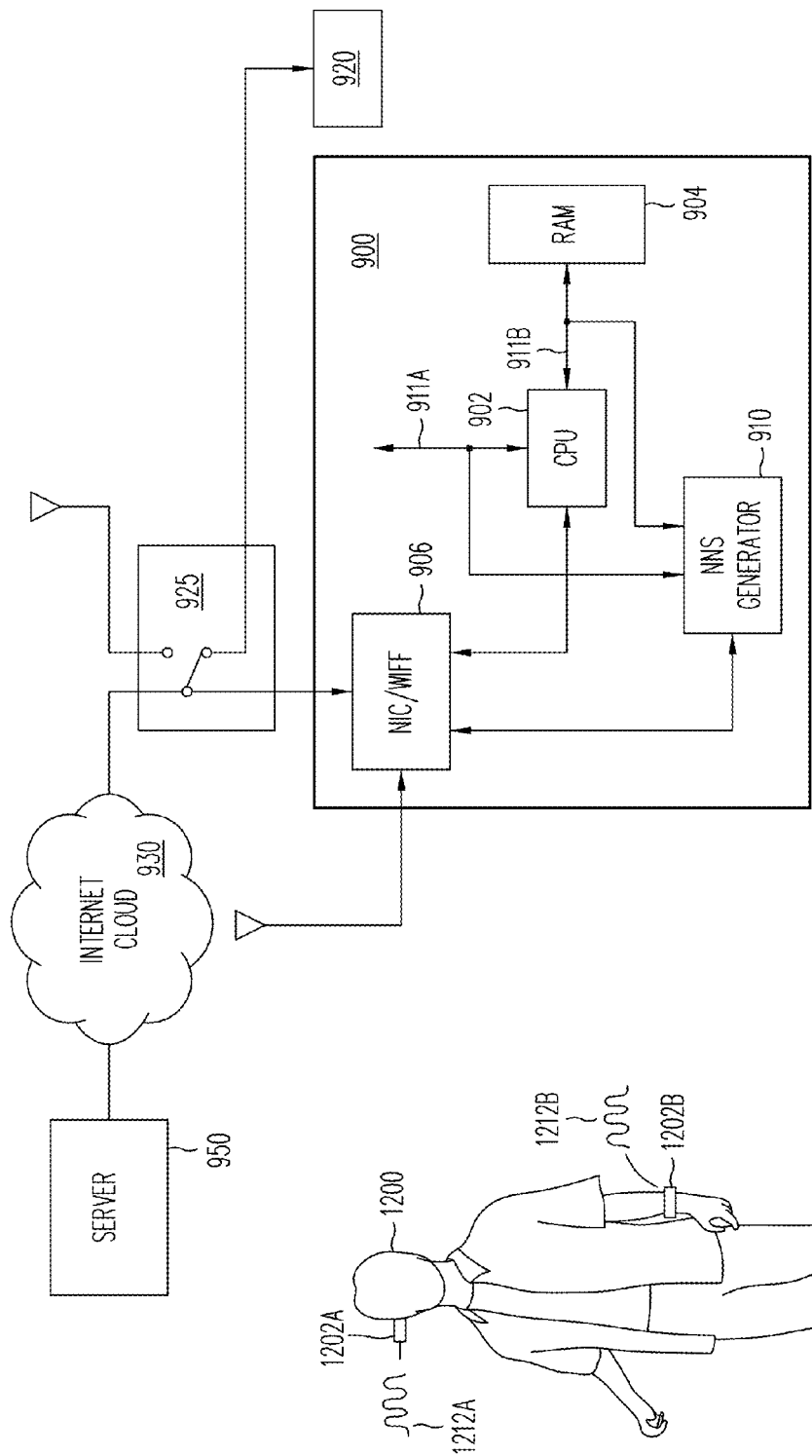

US 9,690,904 B1

SIGNAL-EMBEDDED SIGNATURES

CROSS-REFERENCE TO RELATED APPLICATIONS

The patent application claims the benefit of U.S. Provisional Patent Application No. 61/937,437, entitled SIGNAL-EMBEDDED SIGNATURES, filed on Feb. 7, 2014, by inventor Martin Zizi, incorporated herein by reference as an example of signal-embedded signatures.

This patent application is also a continuation in part and claims the benefit of U.S. patent application Ser. No. 14/292,820, entitled METHODS OF DATA ACQUISITION QUALITY AND DATA FUSION FOR PERSONAL PORTABLE WIRELESS VITAL SIGNS SCANNER, filed on May 30, 2014, by inventors Wenyi Zhao et al., incorporated herein by reference as an example health system with signals having noise to which user identification can be made by noise signature. U.S. patent application Ser. No. 14/292,820 claims the benefit of U.S. provisional patent application No. 61/924,230, filed on Jan. 6, 2014; and further claims the benefit of U.S. provisional patent application No. 61/875,681, filed on Sep. 9, 2013.

FIELD

The embodiments of the invention relate generally to biometrics.

BACKGROUND

One of the main problems in a complex and signal-rich environment is to ascertain the precise origin of any given signal. If we define origin by its physical location then this identification is not problematic as long as there are definite communication channels, say between a signal emitter and a receiver. The wide area network of the Internet or World Wide Web, with its packet-switching protocols, is an example of such a complex but resolved situation.

But even if the physical location or the positive identification of an emitter can be recorded, this does not ensure a well-defined origin when we define origin by the source of the data stream itself.

Numerous situations exist where a measuring system or any system can be fooled about the precise nature or origin of said measurements. Situations like spoofing, phishing, . . . unreliable online identities, all the various strategies to hide the identity of the data, including data forgery or any misleading intent or accidental interference are just a few examples of a near un-limited list of possibilities. The more we are moving towards mobile devices (the web of things, mobile apps for health, remote monitoring, online banking, . . . ), the more likely the risk of having corrupted or non-properly authenticated data.

For years, companies have tried to establish an identity system for users of the Internet or World Wide Web. The basic premise being that users should have a single trusted identity, the incentive for such idea being that it could ease all user interactions offline and online. Microsoft proposed Passport in the late 1990s, but privacy concerns and the FTC made it difficult. Facebook's social graph is another effort. Google+ is another. Google+ is not as much a social site as an 'identity service'. Before Google+, your Google identity was really only used on Google sites. But with Google+ and the +1 button, the identity system can extend across the Internet or World Wide Web. When a user is signed into the Google+ system, his/her information can be tracked. The tracked information helps Google provide more personalized services (like search results) to a user, and also helps with ad targeting to the user.

For secure communication, the banking industry often relied on either secure communication links or complex codes embedded (or not) in the transaction data themselves. Most systems still rely on various levels of keys and/or encryption.

However, problems associated with accidental miss-identification or voluntary/involuntary identity swaps remain. As examples, a bank card or a PIN may be stolen; one may lie; a person's identity may be stolen.

BRIEF SUMMARY

The embodiments are best summarized by the claims that follow below.

With the ever increasing reliance on information and mobile technologies in an ever increasing field of applications, absolute authentication of a user becomes more relevant. Such authentication may apply to devices, inter-device communications or human-device interactions. While actionable solutions exist, a better authentication system should avoid keys, codes, or specific chains of actions.

Biometrics, such as a finger print, offer novel solutions but do not readily protect against mistakes, or willingly misleading inputs. Moreover, they often are difficult in application to information technology (IT) systems themselves. Accordingly, it is desirable to improve upon user identification techniques in order to provide improved security and avoid misidentification.

Use of a noise signature to identify a user can provide a solution. A noise signature is a very specific signature that can be obtained from alternating current (AC) noise in a measured or recorded electrical signal or from a pattern that originates in the measured or recorded electrical signals themselves. The electrical signal that is measured or recorded can be any signal, including those that may originate from a human body of the user and/or from information technology components (e.g., user's cell phone, computer, etc.) associated with the user.

BRIEF DESCRIPTIONS OF THE DRAWINGS

FIG. 1A is an example waveform diagram of electrocardiogram and phonocardiogram of a first user.

FIG. 5A is an example waveform diagram in the time domain of a signal with noise.

FIG. 5D illustrates the final transformed waveform in the frequency domain.

FIG. 6A illustrates an example noisy electrocardiogram signal plot.

FIG. 6B illustrates an example phase plot of the noisy electrocardiogram signal shown in FIG. 6A.

FIG. 9 is a block diagram of an IT system, a computer network with a computer, that generates a noise signature for unique identification of computers communicating over a wide area network or a local area network.

FIG. 10 is a diagram of a user with sensors generating biometric or physiological data streams of data with signal noise from which a human signature may be generated to uniquely identify the user.

DETAILED DESCRIPTION

Figure 1B:
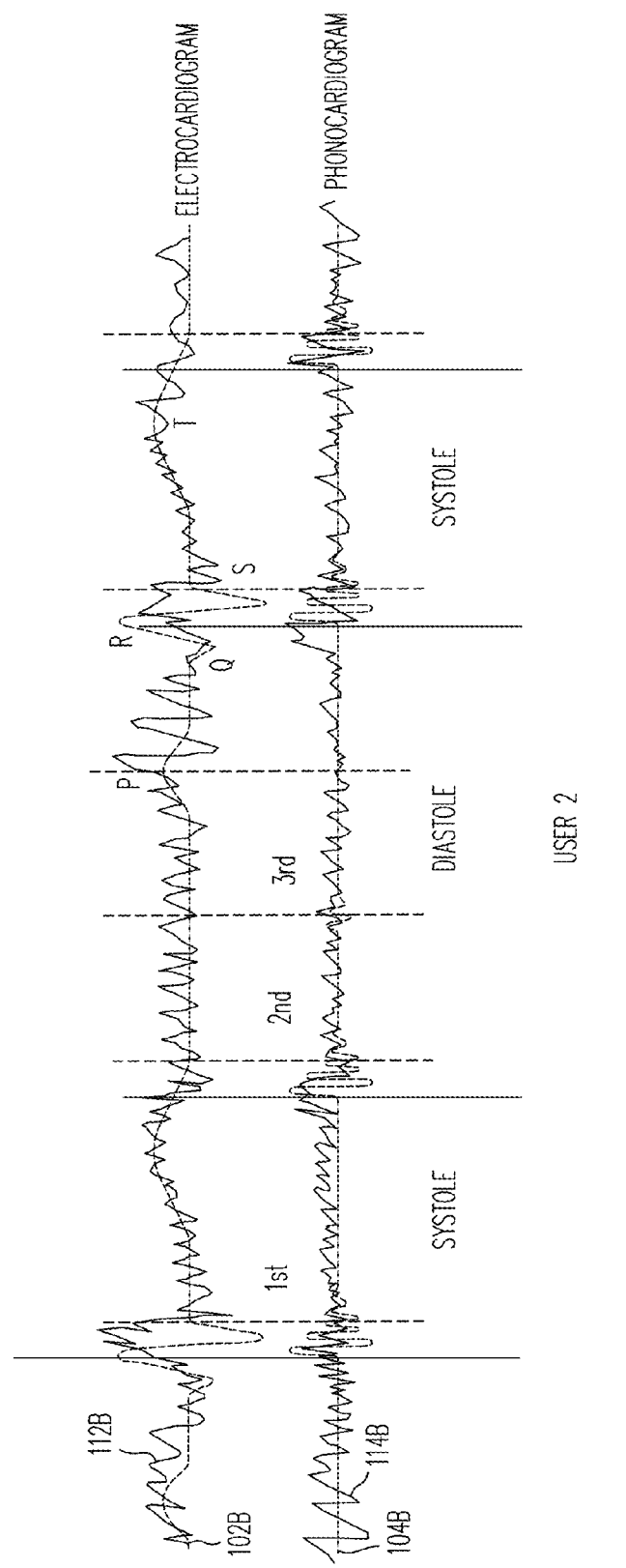
FIG. 1B is an example waveform diagram of electrocardiogram and phonocardiogram of a second user.

In the following detailed description, numerous specific details are set forth in order to provide a thorough understanding of the embodiments. However, it will be obvious to one skilled in the art that the embodiments may be practiced without these specific details. In other instances well known methods, procedures, components, and circuits have not been described in detail so as not to unnecessarily obscure aspects of the embodiments.

The embodiments include methods, apparatus, and systems for forming and using a noise signature.

Note that any organism or structure (e.g., animals, humans, plants, cells, electronic circuits, integrated circuits, processors, etc.) contains molecular variations that are specific to each. The molecular variations between each within the same organism (e.g., human beings) or structure (e.g., electronic circuit) contribute to the electrical signal noise of any electronic signal recordings that can be obtained from those organisms or structures. Thus, electrical signal noise recorded from an organism or structure can provide uniquely identifying information, referred to as a noise signature, about the organism or structure that can be used in a variety of applications. Moreover, the noise signature can be generic, divorced from the recording devices, and thus can be applied even though future devices that may record the noise are unknown.

For example, the noise signature may be applied to vital sign scanning systems, including a personal portable wireless vital signs scanner and the vital signs data that it generates which is described in some detail in U.S. Patent No. 61/924,230 filed Jan. 6, 2014, incorporated herein by reference, as an example vital sign scanning systems, including a personal portable wireless vital signs scanner and personal digital device for which both human noise signatures and machine noise signatures may be formed.

Introduction

In the mobile health sector, the situation with identification problems is different. Given that medical records are of a very intimate nature, they are typically not readily available online over a publicly accessible network, such as the Internet. Medical records have legal, insurance and financial implications, such that highly reliable authentication is important.

Entry ways into medical records is typically by certified health care professionals. The doctor or nurse, after a measurement or a patient conversation, often enters medical data and information into a medical file, transforming them as immutable medical records.

With mobile applications and mobile devices being introduced into the health care system, the risk of misidentification of a patient (such as from low data fidelity) increases. Overburdening health professionals to curate and validate any single digital medical dataset is not even an option. Requiring some form of electronic ID system with or without a card may be viable but remains fragile and far from foolproof given the financial incentives not to be truthful built in the health care systems.

The ideal authentication system would be individual signatures that would be inherently linked to the data streams themselves. Said signatures would not have to be added on top of the data like in the banking example. Said signatures would offer the advantage of being non-dissociable from the data themselves.

One robust and generic solution is to extract identity-specific signatures from the noise in a data stream of data over time in an electrical signal. Any data stream of data with noise in the electrical signal of the data stream may be used to form a noise signature. Of particular interest are data streams of data that are associated with a user, such as data streams of physiological data or data streams of biometrics data. Other data streams of interest are those of machines that generate electrical signals such as user owned computer, cell phone, or electronic device, for example.

Furthermore, forming a noise signature from noise in an electrical signal can be device independent and data agnostic. Any human physiological data stream (e.g., an electrocardiogram (ECG) trace, a respiration wave, etc.) with noise may be used to form a noise signature. The noise signature from a human physiological data stream can be linked to the specific anatomy of each individual. The anatomical variations contribute partly to the noise of the recorded signals and provide a unique signature. Specific biometrics that can be linked to each individual from any biological signal may be used to provide a unique noise signature. The recorded voice or body sounds of a user has specific noises that can identify an individual being may be used to provide a unique noise signature.

In FIG. 10, a human user 1200 is shown having one or more sensors 1202A-1202B to generate data streams of physiological data or biometrics data in analog signals 1212A-1212B. The noise signal in the analog signals 121A-1212B can be used to form a noise signature for the human user 1200.

All information technology (IT) components are not exact copies of each other—they are manufactured and their atomic structures have inherent meso-scale or atomic scale variations. The digital components therein can drive out electrical signals that can generate specific noise signatures. The processor in a computer, for example, drives out electrical signals that may have a specific noise pattern. Accordingly, a unique noise signature associated with the processor may be used for identification purposes amongst a plurality of computers and processors. Calibration includes acquiring a few signals to learn the specific noise patterns linked to a specific IT system. After calibration, a noise signature for the specific IT system can be reliably identified and its source authenticated. The noise signature is applicable throughout a network (e.g., Internet) for any IT system in situations where the IT system is to be identified, as opposed to a user, of the IT system.

FIG. 9 illustrates a computer 900 as an example IT system. The computer 900 includes a processor 202, a storage device 904 (e.g., random access memory and/or other type of memory), and communications cards 906 (e.g., network interface card and Wi-Fi card). Components of the computer may be coupled together via electrical connectors (e.g., wires or printed circuit board traces), such as electrical connectors 911A-911B. The communication cards 906 provide a means of connecting the computer 900 to other computers and servers 950 over a network 930 and to its other computers 920 through switch 925. The network 930 may include at least one of the Internet, the World Wide Web, a wide area network (WAN), or a local area network (LAN), among other networks.

The computer 900 may further include a noise signature (NS) generator 910 coupled to an electrical component of the computer, such as the processor 902. The NS generator 910 monitors one or more unidirectional electrical signals from the processor 902 via the electrical connectors 911A-911B to generate one or more noise signatures of the processor. For example, a unidirectional electrical signal may include a control signal and/or an address signal that is often driven out by the processor to the storage device 904 via electrical connector 911B.

FIG. 5A is an example of a digital electrical signal with noise that may be used. The NS generator 910 of FIG. 9 may use methods described herein to form one or more noise signatures of the processor, for example, so that the computer 900 can be uniquely identified. The noise signature may be coupled to the communications cards 906 (e.g., network interface card and the Wi-Fi card) so that the computer 900 can be uniquely identified over the network 930 (e.g., Internet) to other computers and servers, such as server 950, via wired signals or via wireless signals.

A noise signature can be equally applied to almost any system, whether it is carbon-based (e.g., living organisms) or solid-state based (e.g., an information technology system). A human or living noise signature may be used to identify a human person/user via biometry from the noise in his/her biometric electrical signals. A machine or solid state noise signature may be used to identify IT systems via their noise signature such as an ID tag for the network 930 (e.g., Internet) of networked devices and not for the sake of identifying any user. A noise signature of a networked device or machine perhaps could provide a substitute for IP addresses. Combining both a human noise signature with a machine noise signature can further enhance a positive identification of a user. That is, a carbon based or living noise signature from a carbon based living organism and a machine noise signature from a solid state machine or silicon based system can also be combined or fused together to further enhance user identification.

FIG. 1A is an example waveform diagram of electrocardiogram and phonocardiogram of a first user. FIG. 1A illustrates waveforms 102A,104A, respectively, of example electrical signals of electrocardiogram and phonocardiogram for a first user USER1 over time. Each of the waveforms 102A,104A include noise 112A,114A in the electrocardiogram and phonocardiogram signals. The electrocardiogram and phonocardiogram signals are measured/recorded from the first user USER1. The noise 112A, 114A in the electrocardiogram and phonocardiogram signals can be used to generate one or more unique first noise signatures of the first user USER1.

FIG. 1B is an example waveform diagram of electrocardiogram and phonocardiogram of a second user. FIG. 1B illustrates waveforms 102B,104B, respectively, of example electrical signals of electrocardiogram and phonocardiogram for a second user USER2 over time. Each of the waveforms 102B,104B include noise 112B,114B in the electrocardiogram and phonocardiogram signals. The electrocardiogram and phonocardiogram signals are measured/recorded from the second user USER2. The noise 112B, 114B in the electrocardiogram and phonocardiogram signals can be used to generate one or more unique second noise signatures of the second user USER2.

Amongst a plurality of stored noise signatures, the first noise signature may be used to identify the first user and the second noise signature may be used to identify the second user.

While FIGS. 1A and 1B illustrate analog electrical signals 102A-102B, 104A-104B that may be used to extract a noise signature, the system may also use a digital electrical signal with noise (e.g., illustrated by FIG. 5A) to extract a unique noise signature associated with a user for identification purposes.

The system may use a noise signature in potential applications when and wherever authentication is needed, such as remote sensing, mobile health care, network connections (e.g., Internet or World Wide Web connections), secure logins, or wherever biometrics are used to provide secure access.

Extracting and Storing a Noise Signature

Figure 2:
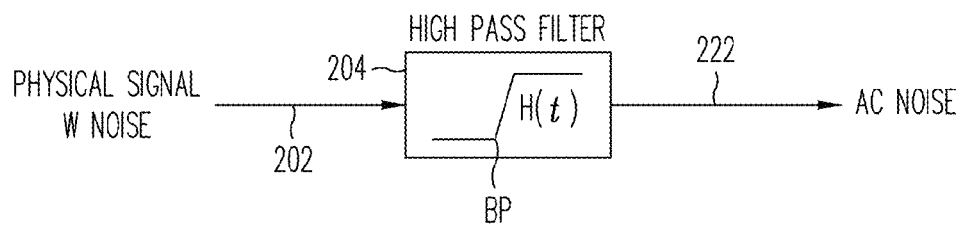
FIG. 2 is a block diagram of a high-pass filter for filtering out a signal and emphasizing noise.
Figure 3:
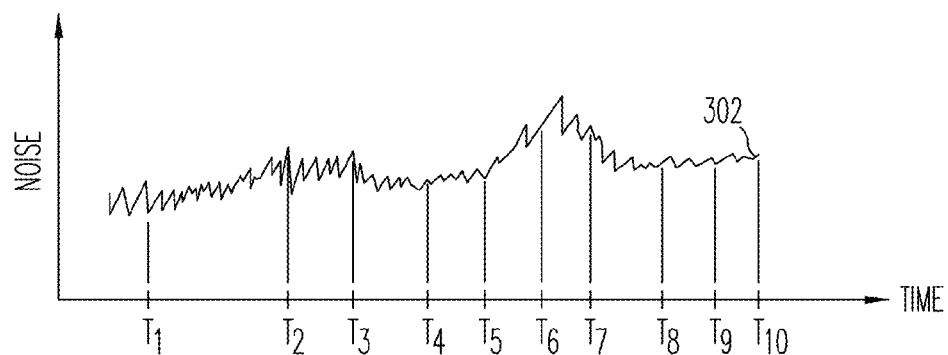
FIG. 3 is an example waveform diagram of the AC noise that is sampled periodically to obtain a noise signature.
Figure 8A:
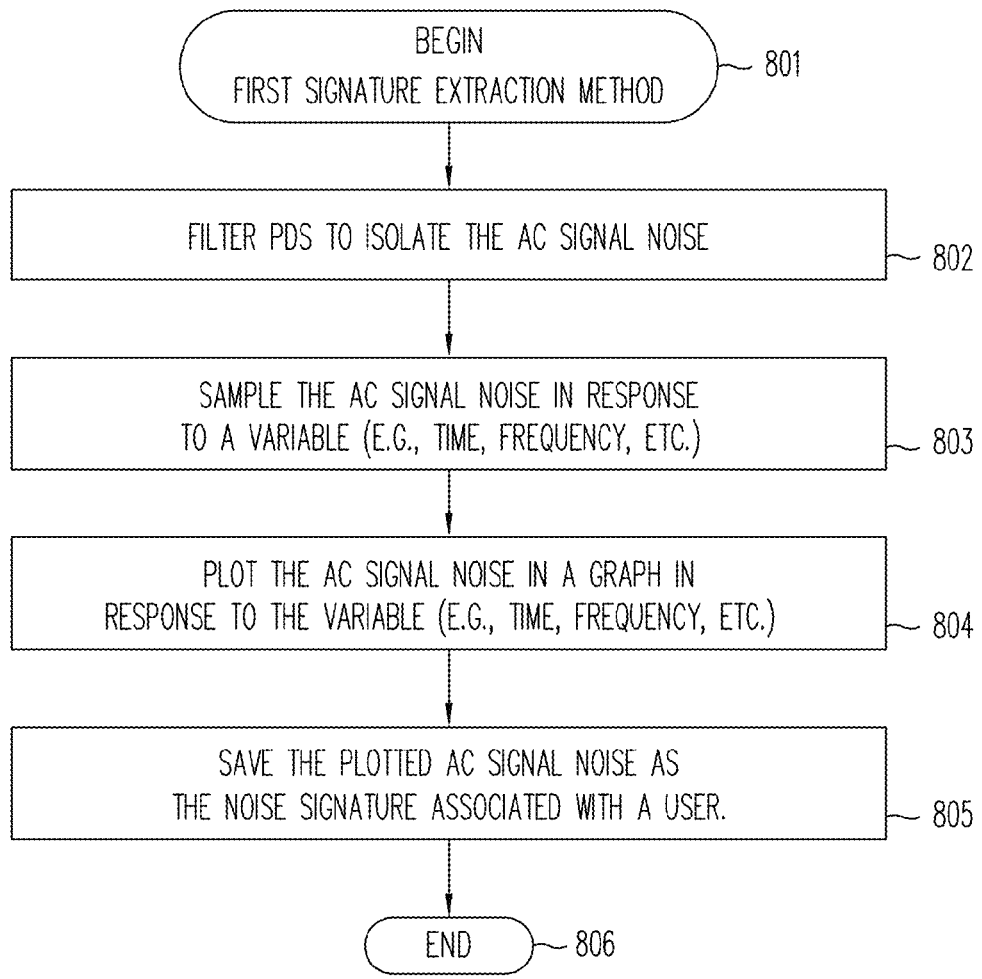
FIG. 8A is a flow chart of a first method for extracting a noise signature.

A number of methods and systems may be used to extract a unique noise signature from an electrical signal. FIGS. 2-3 and 8A illustrate a first example method, while FIGS. 5A-5D and 8B illustrate a second example method.

FIG. 8A is a first example method of extracting a signature. The method begins with block 801 and goes to process block 802.

At process block 802, the system filters an electrical physiological data signal (PDS) by using a filter to isolate the AC signal noise.

FIG. 2 illustrates a block diagram of a high-pass filter for filtering out a signal and emphasizing noise, for a first method of extracting a noise signature from a signal. A physiological signal 202, such as an electrocardiogram (ECG) signal, is coupled into a high-pass filter 204.

The filter response H(t) of the high-pass filter 204 filters out DC and low frequency signals below the pass band frequency so that the AC noise 222 with frequencies in the pass band are formed at the output of the filter.

The filter response H(t) of the high-pass filter 204 filters out DC and low frequency signals below the pass band frequency so that the AC noise 222 with frequencies in the pass band are formed at the output of the filter.

At process block 803 of FIG. 8A, the system samples the AC signal noise in response to a variable (e.g., time, frequency, phase, etc.).

FIG. 3 shows an example waveform diagram 302 of the AC noise 222 that is output from the high-pass filter 204. The AC noise waveform 302 is periodically sampled at different predetermined times to obtain values for a noise signature.

At process block 804, the system plots the sampled AC signal noise in a graph in response to the variable (e.g., time, frequency, phase, etc.) at the respective predetermined times.

Figure 4:
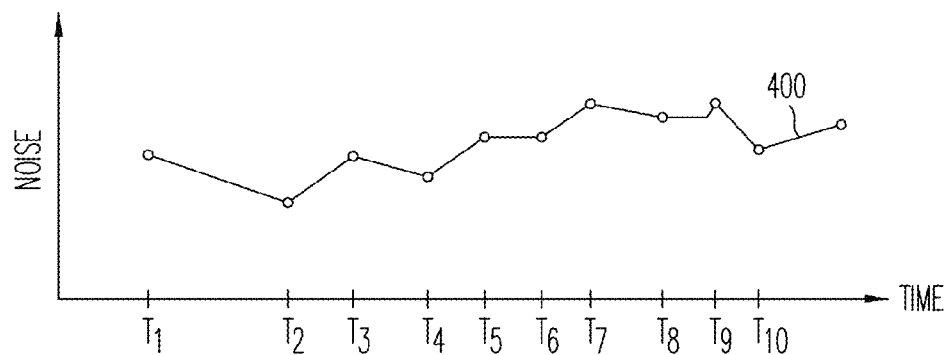
FIG. 4 is a plot of sampled AC noise that may be used to form a noise signature.

FIG. 4 shows a plot of the sampled values of the noise at the sample times T1 through T10.

At process block 805, the system stores the plotted sampled values of the AC signal noise as the noise signature associated with a given known user (e.g., first user). A known user is a user for which the system has access to profile information (e.g., name, address, phone number, account number, and/or social security number, etc.). The system may use a mathematical algorithm to represent the noise signature compactly. At process block 806, the system may conclude or repeat the method.

Figure 5B:
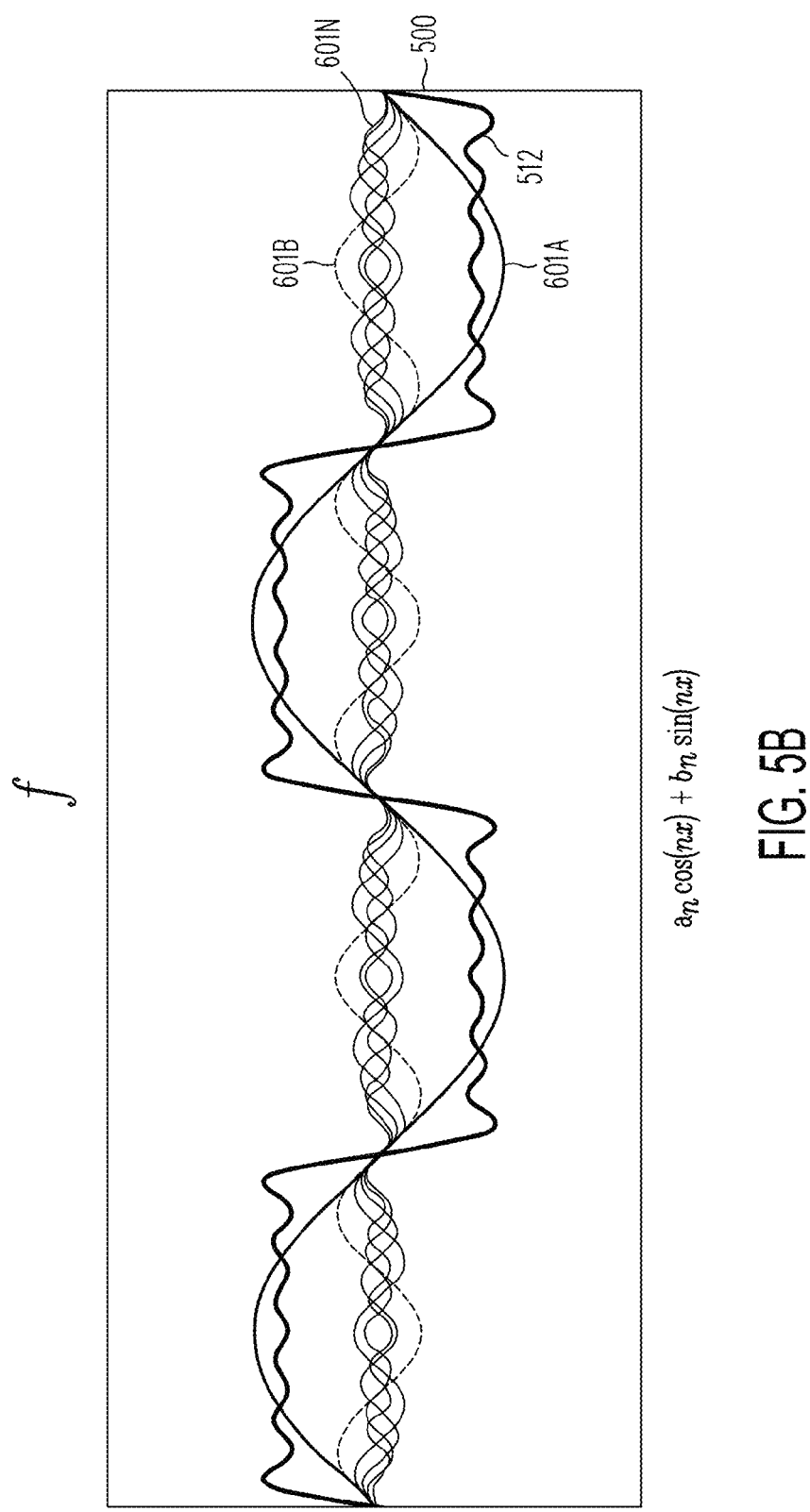
FIG. 5B is an example waveform of FIG. 5A with composite waveforms superimposed thereon.

FIGS. 8B and 5A-5D show a second method for extracting a noise signature. FIG. 5A shows an example digital electrical signal 500, such as generated by a user's electronic device (e.g., a cell phone, a health scanner, or computer). The digital electrical signal 500 includes signal noise 512 that is unique to the user's electronic device and the user, for so long as he/she controls and/or owns the electronic device. It desirable to extract the signal noise 512 and represent it as a noise signature to identity the user's electronic device that is owned and under control by a given user.

FIG. 6A shows an example noisy ECG signal 900 (an analog electrical signal) with signal noise 912.

The signal noise 512 may be isolated from the signal 500 initially or it may be processed together with the signal and later sampled out. FIG. 7B includes blocks 3-4 that isolate the signal noise before extraction of the signature. In any case, the following method may be used for signature extraction.

Referring again to FIG. 8B, the method begins with block 851 and goes to process block 852. At process block 852, the system transforms the signal noise 512, 912 (with or without the underlying digital signal or analog signal) in the time domain into the frequency domain to generate a power density spectrum of the signal noise (with or without the underlying digital signal or analog signal). Mathematically, the system may perform this transformation by using a Fourier Transform including the equation $$\hat{f}(\xi) = \int_{-\infty}^{\infty} f(x) e^{-2\pi i x \xi} \, dx,$$

where ξ represents real frequency (in hertz) values and the independent variable x represents time), the transform variable. Using software or digital circuits that can digitally sample a signal, the system may use a discrete-time Fourier Transform (DFT) including the equation $$X_k = \sum_{n=0}^{N-1} x[n] \cdot e^{-i 2\pi \frac{kn}{N}}.$$

Figure 5C:
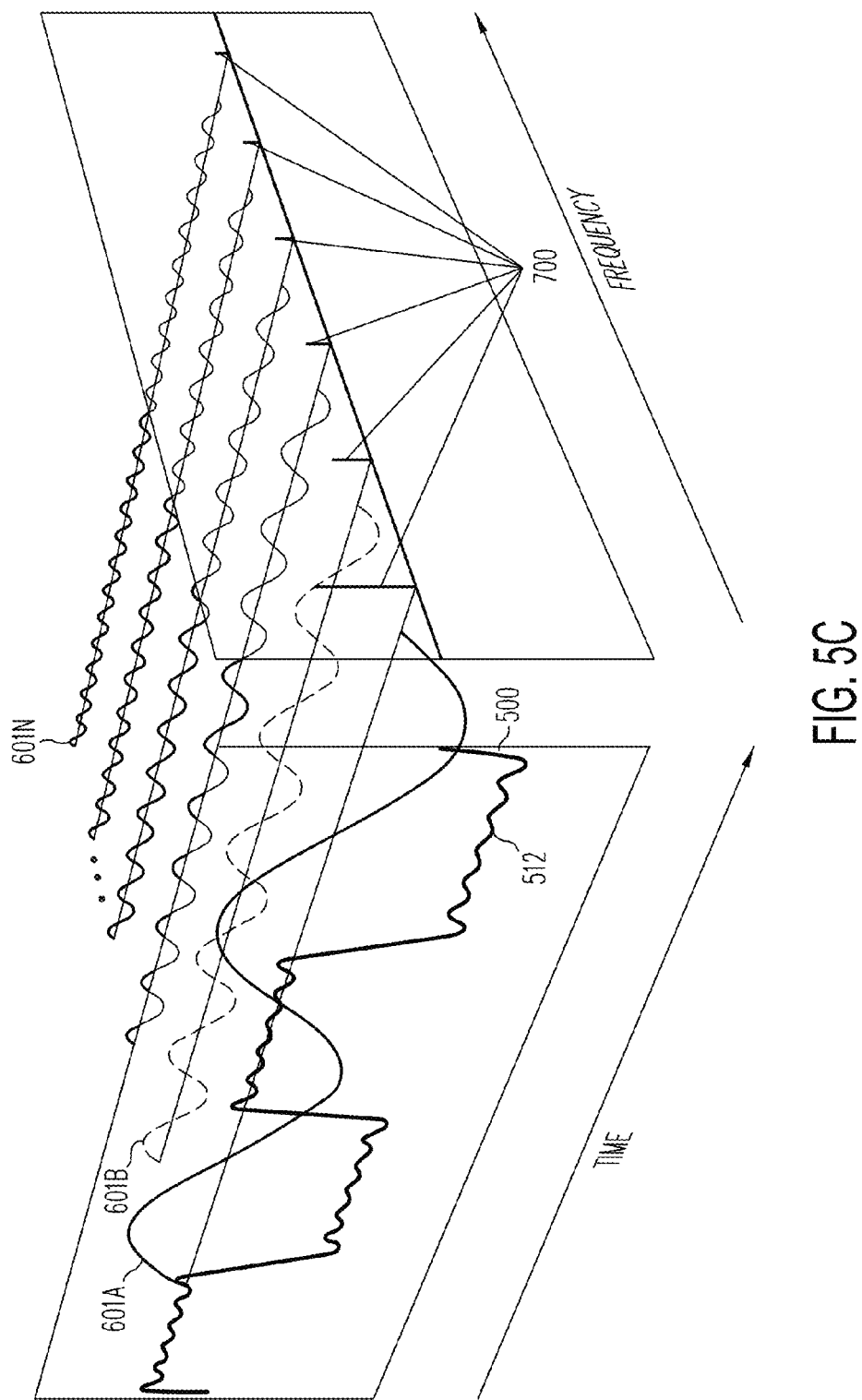
FIG. 5C is a three dimensional view illustrating the transformation from the time domain to the frequency domain for the example waveform shown in FIG. 5A.

As shown by FIGS. 5B and 5C, the Fourier Transform in essence tries to represent the signal noise 512, 912 (with or without the underlying signal) into N component frequency parts with N sine or cosine waveforms 601A-601N of appropriate phase, frequency, and amplitude, where N is a positive integer. The Fourier Transform can form a power spectral density curve 700 for the signal noise (with or without the underlying signal), as shown in FIG. 5C.

Figure 8B:
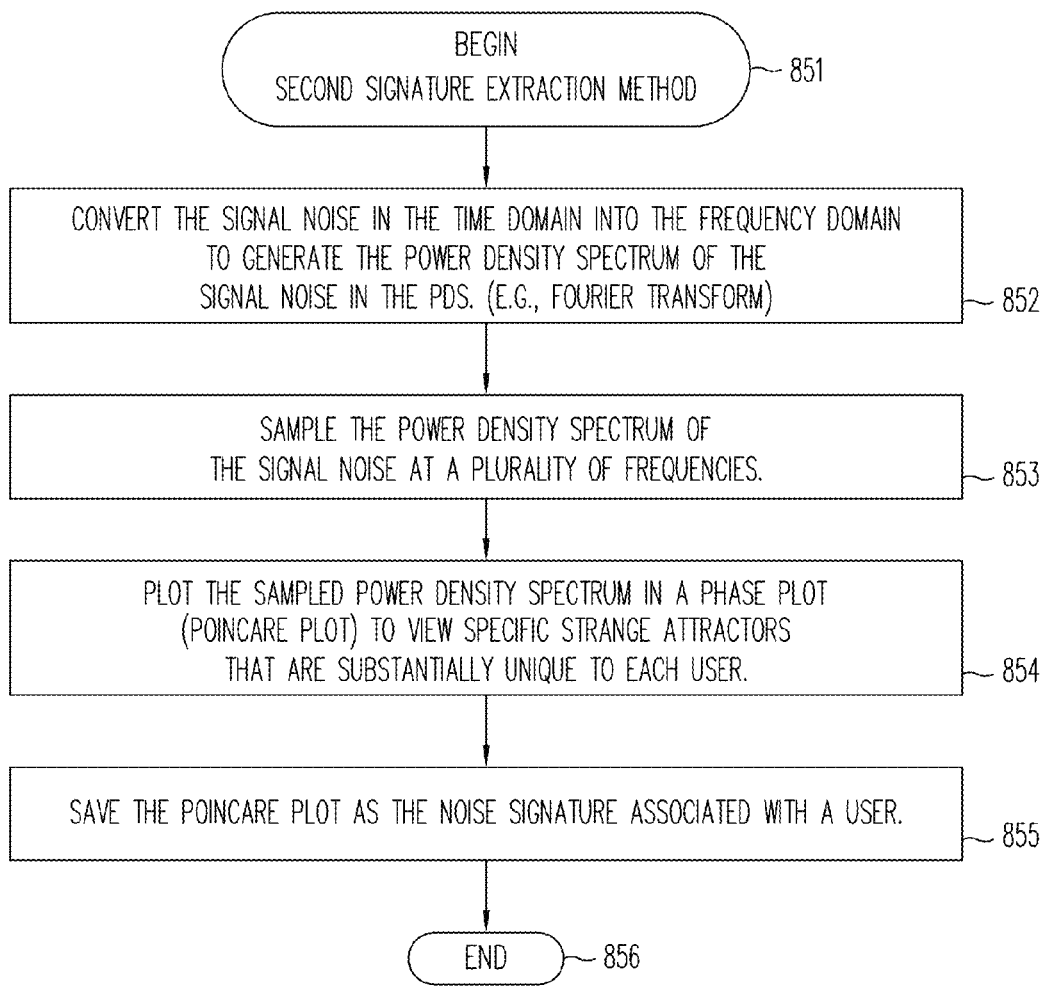
FIG. 8B is a flow chart of a second method for extracting a noise signature.

At block 853 of FIG. 8B, the system samples the power density spectrum of the signal noise at a plurality of frequencies. Knowing the underlying frequency of the signal, its frequency may not be sampled. Thus, the signal noise can be isolated therefrom.

In FIG. 5D, the system may discard the first sample 801, for example, to avoid the base frequency of the signal. Samples 812A-812M are samples at frequencies of the signal noise that the system may use to generate the noise signature.

At process block 854 of FIG. 8B, the system plots the sampled power density spectrum in a phase plot (Poincare Plot) to provide a view of specific strange attractors that are substantially unique to each user.

FIG. 6B illustrates an example phase plot 1000 of both signal 900 and noise 912 of FIG. 6A. The large transitions of the signal 900 of FIG. 6A are represented by the outer rings 1002 in the phase plot 1000 of FIG. 6B. The signal noise 912 is represented by the grouping 1012 nearer zero between −0.5 and 0.5 along the X axis. The grouping 1012 can be magnified and extracted from the outer rings 1002 to represent the noise signature. Alternatively, excluding the signal from the sampling of the power spectra density will amplify the grouping 1012 so that it can be readily stored as the noise signature.

At block 855 of FIG. 8B, the system associates the phase plot of the noise signal (e.g., the grouping 1012) with the user. The system stores the phase plot as the noise signature of the user.

At block 856 of FIG. 8B, the signature extraction method may conclude.

Using a Noise Signature to Identity of a User

Figure 7A:
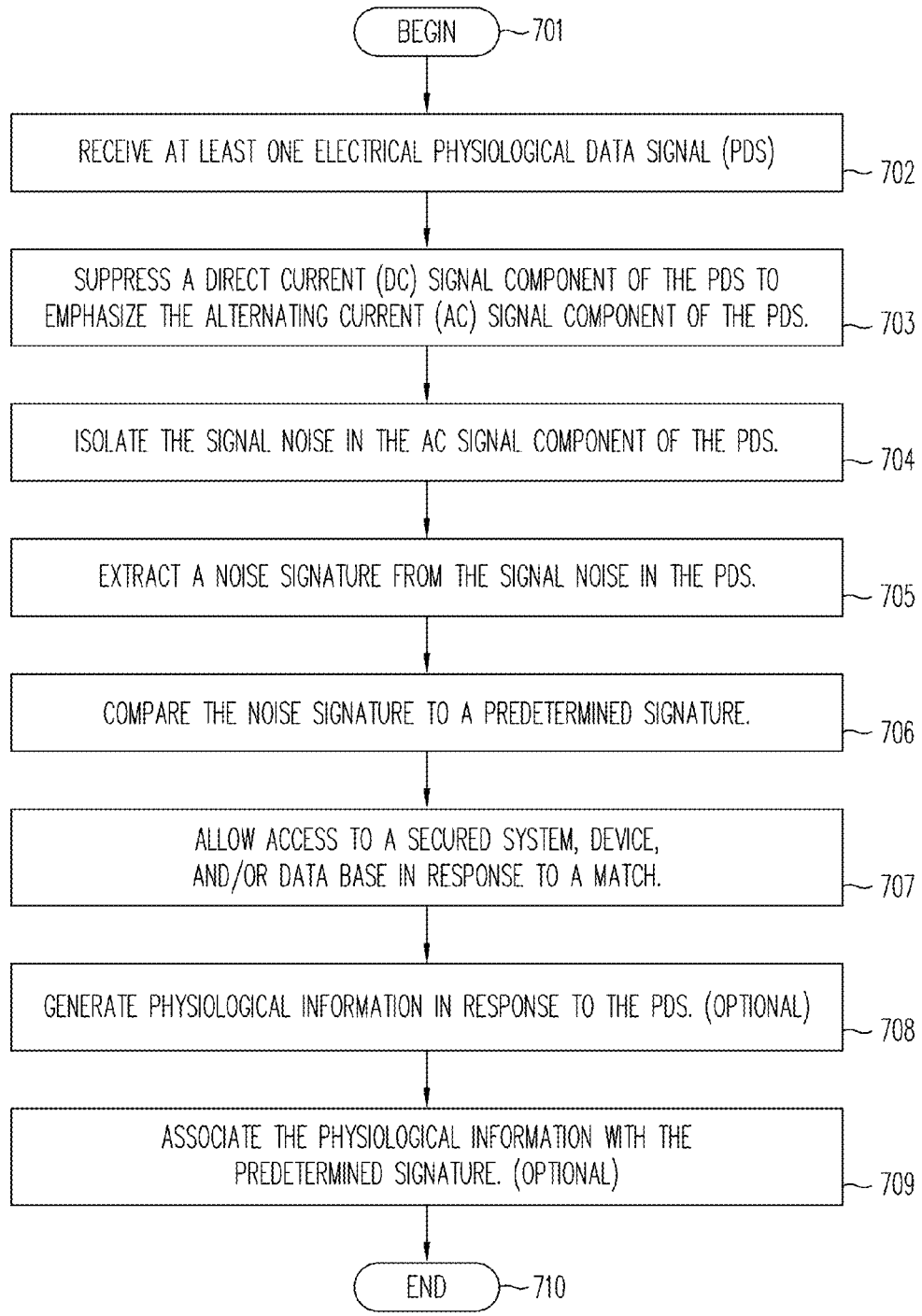
FIG. 7A is a flow chart of a first method for using a noise signature.
Figure 7B:
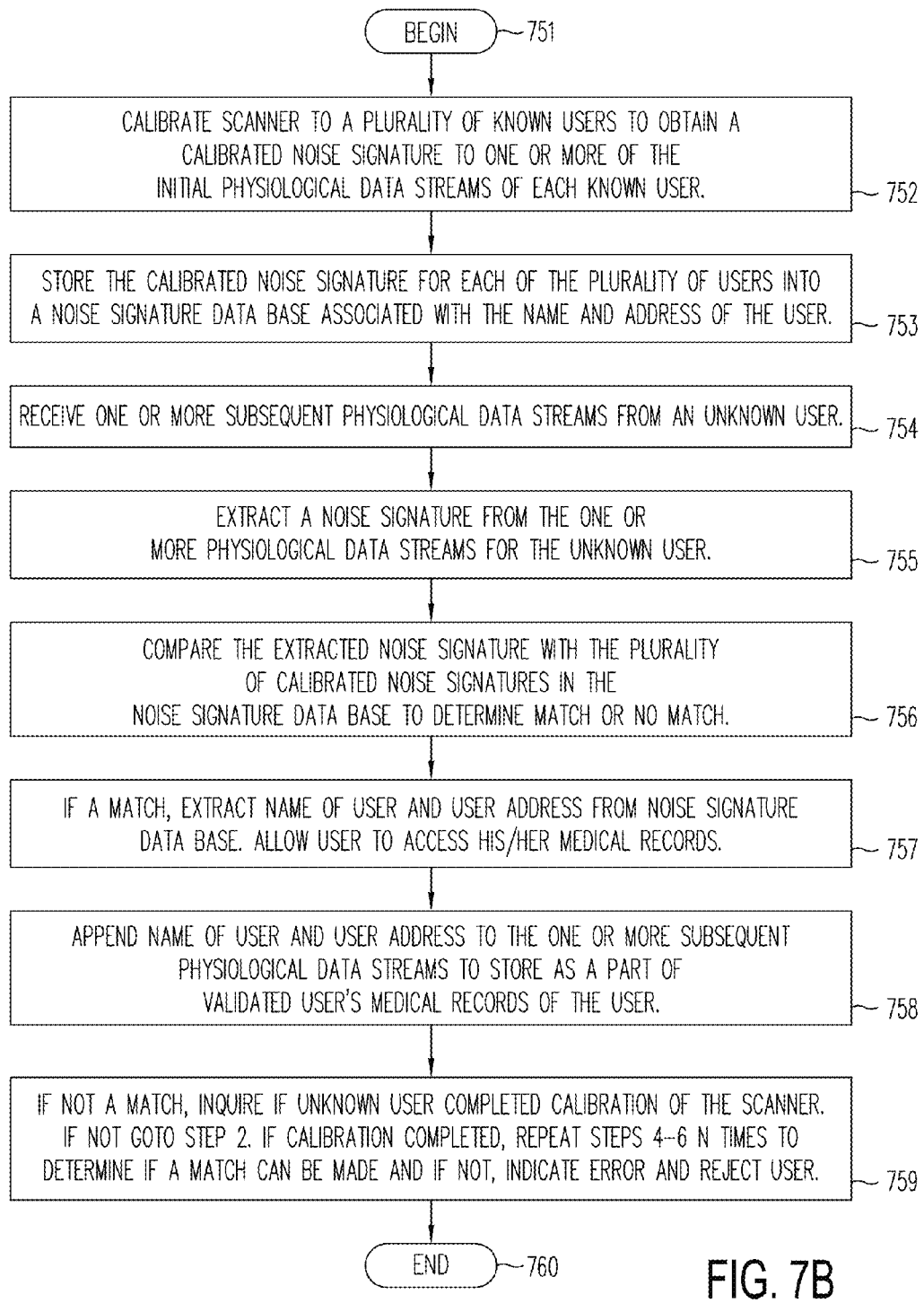
FIG. 7B is a flow chart of a second method for using a noise signature.

FIG. 7A is a first example method for a using a noise signature. The method begins with block 701 and goes to block 702.

At process block 702, the extraction system receives at least one electrical physiological data signal (PDS).

At process block 703, the system suppresses a direct current (DC) signal component of the PDS to emphasize the alternating current (AC) signal component of the PDS.

At process block 704, the system isolates the signal noise in the AC signal component of the PDS from the PDS. The system may use a filter, such as that shown in FIG. 2, to perform at least the following: suppress the DC signal components, emphasize the AC signal component, and isolate the signal noise in the AC signal component.

At process block 705, the system extracts a noise signature from the signal noise in the PDS. In accordance with one aspect of one embodiment, the system may sample the signal noise in the PDS periodically, as described with reference to FIG. 3. In accordance with one aspect of one embodiment, the signal noise in the PDS may undergo the following: a Fourier transform, a sample, and/or a phase plot to extract a second noise signature for comparison, as described with reference to FIGS. 5A, 5B, 6A, and 6B for example.

At process block 706, the system compares the second noise signature to known predetermined noise signatures stored in a database in order to determine a match to a known user.

At process block 707, if the system finds a match, then the system provides access to a secured system, device, and/or database. If a match is not found, then the system repeats the process of FIG. 7A or indicates an error.

At process block 708, optionally if the system receives an PDS signal, then the system generates physiological information in response to the PDS. Otherwise, the system may skip process blocks 708 and 709.

At process block 709, the system stores and associates the generated physiological information with the known user and the user's predetermined noise signature.

At process block 710, the system may conclude the process, repeat the process for a next user, or repeat the process for the same user but with a different data stream.

The system may use a noise signature in potential applications when and wherever authentication is needed, such as remote sensing, mobile health care, Internet or World Wide Web connections, secure logins, or wherever biometrics are used to provide secure access. Accordingly, the system can apply a noise signature to the fields of mobile human health/wellness, IT interconnectivity, security, and health screening for some defective conditions in living organisms (e.g., Parkinson, stress, heart valve defects, etc.) or in IT components (e.g., quality control, remote wear-and-tear sensing, etc.).

FIG. 7B is a second example method for using a noise signature. The method begins at block 751 and goes to block 752.

At process block 752, the system uses a known user to calibrate the scanner to obtain a calibrated noise signature associated with the known user. The system also uses a plurality of known users to calibrate a scanner for each user to obtain a calibrated noise signature for each user. The system may use one or more initial physiological data streams of each known user to generate each calibrated noise signature. The process for generating the calibrated noise signature may be similar to that described herein regarding noise signature extraction.

At process block 753, the system stores the calibrated noise signature for each of the plurality of users into a noise signature database associated with profile information (e.g., name, address, phone number, account number, and/or social security number, etc.) for each user.

After calibration, the scanner can be used to identify a user when subsequent scans and data streams are generated. A health scanner may be used by one or more persons or at least scan one or more persons for vital signs.

At process block 754, a processor in the scanner receives one or more subsequent physiological data streams from a user that has yet to be identified, the user is currently an unknown user (e.g., second user). An unknown user is a user for which the system does not have access to profile information.

At process block 755, the system extracts a noise signature from the one or more physiological data streams for the unknown user.

At process block 756, the system compares the extracted noise signature to the plurality of calibrated noise signatures that are stored in the noise signature database. This comparison step is to determine whether there is a match or no match of the extracted signature to the calibrated signature of known users in the database. If no match the process goes to process block 759, skipping process blocks 757-758. If a match the process goes to process block 757.

At process block 757, if a match, the system reads the profile information for the user from the noise signature database. If a match, the system may allow the user to access, review, and/or copy the user's medical records at a medical records database.

At process block 758, the system may append the profile information to the one or more subsequent physiological data streams so that the system may store the profile information as a part of the validated user's medical records. The system then skips process block 759 and goes to process block 760 to conclude or repeat for a next scanning session by the same user or another user.

At process block 759, if there was no match, the system may ask the unknown user if he/she completed calibration of the scanner. If the calibration was not completed, then the system may go to process block 752. However, if the calibration was completed, then the system may repeat process blocks 754-756 N times to determine if a match can be made or not, where N is a positive integer. If the scanner still determines that there is no match with the incoming noise signature against those stored in the database, then the system may indicate an error, reject the unknown user, and refuse user access to any secure record.

CONCLUSION

When implemented in software, the elements of the embodiments are essentially the code segments of instructions that may be executed by one or more processors to perform and carry out tasks and provide functionality. The program or code segments can be stored in a processor readable medium or storage device are coupled to or at least in communication with the one or more processors. The processor readable medium may include any medium or storage device that can store information. Examples of a processor readable medium include, but are not limited to, an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The program or code segments may be downloaded or transmitted by a computer data signal embodied in a carrier wave over a transmission medium or communication link. A computer data signal may include any signal that can propagate over a transmission medium such as electronic network channels, optical fibers, air, electromagnetic, RF links, etc. The program or code segments may be downloaded, for example, over computer networks such as the Internet, an intranet, etc.

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination.

Accordingly, while certain example embodiments have been particularly described and shown in the accompanying drawings, they should not be construed as limited by such embodiments, but rather construed according to the claims that follow below.

What is claimed is:

1. A method for a health scanning system, the method comprising:
    receiving an initial physiological data stream for a known user;
    calibrating a scanner to the known user to obtain a calibrated noise signature for the initial physiological data stream of the known user;
    storing the calibrated noise signature for the known user into a noise signature database associated with profile information for the known user;
    receiving a subsequent physiological data stream from an unknown user;
    extracting a noise signature from the subsequent physiological data stream for the unknown user; and
    comparing the extracted noise signature with the calibrated noise signature in the noise signature database to determine a match or no match;

wherein a match is determined for the unknown user to validate as the known user and the method further includes
   extracting the profile information from the noise signature database for the known user;
   allowing the unknown user to access user medical records associated with the known user; and
   appending the profile information to the subsequent physiological data stream to store as a part of the user medical records associated with the known user.

2. The method of claim 1, wherein the profile includes at least one of:
   a name;
   an address;
   a phone number;
   an account number; or
   a social security number.

3. The method of claim 1, where no match is determined and the method further comprises:
   determining the unknown user did not complete a calibration of the scanner; and
   calibrating the scanner for the unknown user.

4. The method of claim 1, wherein no match is determined and the method further comprises:
   determining the unknown user completed a calibration of the scanner; and
   repeating the following steps one or more times to determine if a match can be made:
      the receiving of a subsequent physiological data stream,
      the extracting of a noise signature, and
      the comparing of the extracted noise signature.

5. The method of claim 1, wherein no match is determined and the method further comprises:
   indicating an error; and
   rejecting the unknown user.

6. The method of claim 1, wherein
   the calibrated noise signature is due to molecular variations in the known user, and
   the known user is a human being.

7. The method of claim 1, wherein a match is determined and the method further comprises:
   allowing access to at least one of a secured system, a secured device, or a secured database.

8. The method of claim 1, further comprising:
   suppressing a direct current (DC) signal component of the physiological data stream to emphasize an alternating current (AC) signal component of the physiological data stream;
   isolating a signal noise in the AC signal component of the physiological data stream; and
   extracting a noise signature from the signal noise to form the calibrated noise signature.

9. The method of claim 1, further comprising:
   generating physiological information in response to the physiological data stream; and
   associating the physiological information with the calibrated noise signature.

* * * * *